United States Patent [19]

Dötzer et al.

[11] 4,144,140

[45] * Mar. 13, 1979

[54] METHOD FOR THE PREPARATION OF ADDITIVES IN ORGANO-ALUMINUM ELECTROLYTE MEDIA

[75] Inventors: Richard Dötzer, Nuremberg; Hans-George Hauschildt, Erlangen, both of Fed. Rep. of Germany; Enno Todt, deceased, late of Erlangen, Fed. Rep. of Germany, by Susanne Todt, Ruth K. Todt, Ernst J. Todt, heirs, Erlangen, Fed. Rep., Germany

[73] Assignee: Siemens Aktiengesellschaft, Munich, Fed. Rep. of Germany

[ * ] Notice: The portion of the term of this patent subsequent to Jun. 28, 1994, has been disclaimed.

[21] Appl. No.: 873,079

[22] Filed: Jan. 27, 1978

Related U.S. Application Data

[62] Division of Ser. No. 630,949, Nov. 13, 1975, Pat. No. 4,071,526.

[30] Foreign Application Priority Data

Nov. 13, 1974 [DE] Fed. Rep. of Germany ....... 2453829

[51] Int. Cl.$^2$ .......................... C25D 3/02; C25D 3/44
[52] U.S. Cl. ............................. 204/14 N; 204/DIG. 2

[58] Field of Search ................ 204/14 N, 39, DIG. 2, 204/14 R

[56] References Cited

U.S. PATENT DOCUMENTS 4,032,413  6/1977  Dotzer et al. ..................... 204/14 N

*Primary Examiner*—T. M. Tufariello
*Attorney, Agent, or Firm*—Kenyon & Kenyon, Reilly, Carr & Chapin

[57] ABSTRACT

The invention concerns a method for the preparation of additives for influencing the electrocrystalline growth in aprotic oxygen- and water-free organo-aluminum electrolyte media. A compound which contains a sulfonimide or sulfonamide group as the reactable group, preferably, N-benzoylbenzenesulfonimide, optionally in the presence of an inert organic solvent, is reacted with at least one organoaluminum compound of the general formula $AlR_3$, where R is an alkyl radical, in the ratio of 1:1 to 1:6.

The additives obtained furnish a bright aluminum coating on metals and conductive materials in direct electrodeposition.

1 Claim, No Drawings

METHOD FOR THE PREPARATION OF ADDITIVES IN ORGANO-ALUMINUM ELECTROLYTE MEDIA

This is a division of application Ser. No. 630,949 filed Nov. 13, 1975 now U.S. Pat. No. 4,071,526.

BACKGROUND OF THE INVENTION

This invention is concerned with a method for the preparation of additives for influencing the electrocrystalline growth in aprotic oxygen- and water-free organo-aluminum electrolyte media, which is characterized by the feature that a compound, which contains a sulfonimide or sulfonamide group as the reactable group, is reacted with at least one organo-aluminum compound of the general formula $AlR_3$, where R is an alkyl radical, particularly ethyl, in the molar ratio of from about 1:1 to 1:6. The reaction takes place preferably in the presence of an inert organic solvent such as, for instance, toluene or xylene.

Suitable sulfonimides are, for example:

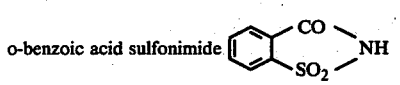

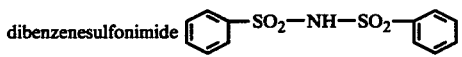

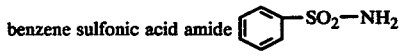

o-Benzoic acid sulfonimide and N-benzoylbenzenesulfonimide have been found to be particularly suitable reaction components.

In a concentration range of 10 to 100 g/l of this additive of o-benzoic acid sulfonimide and aluminum triethyl, a brightness (reflectivity) of 80% was obtained, i.e., the reflectivity corresponded to about 80% of that of a silver mirror.

The reaction is performed by apportioned addition of the aluminum trialkyl, diluted with an organic solvent, to the organic, sulfonimide group-containing compound. Temperatures of up to about 100° C., and preferably, of about 70° to 80° C., should be used in order to avoid local overheating through an exothermic reaction of the reaction partners. Because of the chemical properties of the aluminum alkyl compounds, the reactions must be performed in a dry inert gas, i.e., with the exclusion of air and moisture.

Suitable organo-aluminum compounds are aluminum trialkyls, preferably with alkyl radicals from $C_1$ to $C_4$. Particularly well suited is aluminum triethyl. The additives, i.e., the brighteners, may also be isolated from the solution as defined compounds.

The additives obtained in accordance with the invention act as brighteners or inhibitors of crystalline growth with aprotic, oxygen-and water-free organo-aluminum electrolyte media. If added in solid form, or preferably, in solution, they make possible the electro-deposition of aluminum on metals and conductive materials in shiny or mirror-like form. Particularly well suited is the additive obtained from 1 mole o-benzoic acid sulfonimide and 2 moles aluminum triethyl. The additives as well as the organo-aluminum electrolyte can be dissolved in inert, water-free aprotic solvents, e.g., xylene or toluene. Through the use of the additives prepared by the method according to the invention, in organo-aluminum electrolytes, one obtains a highly-adhering, shiny and mirror-like aluminum deposit directly on metals and conductive materials.

The bright aluminum layers produced, using the additives prepared in accordance with the invention, find use as mirrors and reflectors for light and heat radiators as well as for decorative purposes and for corrosion protection, and in general for surface finishing. If required, the layers can also be coated with a hard, electrically insulating layer by means of anodic oxidation, and/or stained.

The invention will be explained in further detail by means of the following examples.

EXAMPLE 1

In a dry inert gas ($N_2$ or Ar), 55 g. (0.3 mole) of finely divided o-benzoic acid sulfonimide is suspended in 500 ml toluene in a 2-liter three-neck flask, provided with a stirrer, dropping funnel and oil-operated reflux cooler, and heated to 80° C. in an oil bath. To the suspension are added drop-wise over a period of 2 hours, at room temperature, 68.5 g (0.6 mole), corresponding to 85 ml $Al(C_2H_5)_3$, dissolved in 85 ml toluene. The reaction solution is initially colored yellow, later orange-brown, and finally remains greenish-yellow. Subsequently, the solution is kept at 80° C. (oil bath) for another 2 hours, while stirring. Then the reaction solution is evaporated under reduced pressure at 40° to 60° C. to about 130 to 150 ml. The greenish-yellow brightener solution can be stored for many weeks if air and moisture are kept out.

With this solution, if added as an additive to an organo-aluminum electrolyte medium, a bright aluminum coating with a reflectivity of 70 to 80% of that of a silver mirror is obtained.

From this brightener solution, a compound of the formula

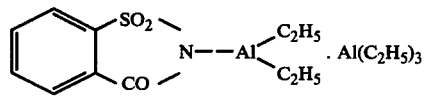

can be isolated, which can be called an aluminum triethyl solvate or a coordination compound of the aluminum triethyl with N-(diethyl aluminum)-o-benzoylsulfonimide. For this compound, the following analysis was obtained: Al, 14.71%; N, 3.78%; S, 8.99%. This corresponds to an atomic ratio of Al:N:S = 2.00:1.00:1.04.

EXAMPLE 2

As in example 1, o-benzoic acid sulfonimide is reacted with $Al(C_2H_5)_3$ dissolved in toluene, in the molar ratio 1:1.25, i.e., 18.3 g. O-benzoic acid sulfimide (0.1 mole) with 14.3 g. aluminum triethyl (0,125 mol). One obtains 12.7 g. (95% of theoretical) N-(diethyl aluminum)-o-benzoyl sulfonimide of the formula

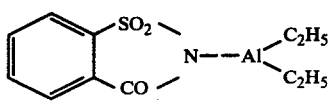

Analysis: Al, 9.92%; N, 5.46%; S, 11.93%. This corresponds to an atomic ratio Al:N:S of 1.00:1.06:1.01.

EXAMPLE 3

As in Example 1, o-benzoic acid sulfonimide is reacted with aluminum triethyl in a molar ratio of 2:1, i.e., 18.3 g. o-benzoic acid sulfonimide (0.1 mol) with 5.7 g. aluminum triethyl (0.05 mole). One obtains 19.2 g. (91% of theoretical) of di-(o-benzoylsulfonimide)-ethyl aluminum of the formula as a crystalline substance.

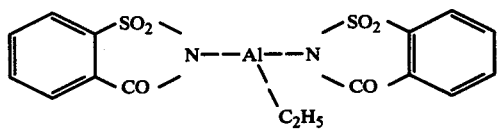

Analysis: Al, 5.46%; N, 5.82%; S, 12.95%. This corresponds to an atomic ratio Al:N:S of 1.00:2.06:1.99.

The reflectivity (brightness) of the aluminum is always measured with a modified Universal Measuring Equipment of the firm Dr. Bruno Lange, Berlin. The principle of the reflectivity measurement is the reflection of a light beam at the surface of the object to be tested, the angle of incidence and the angle of reflection of the light beam being equal. The reflected light is measured by means of a photocell and is indicated via a light galvanometer.

What is claimed is:

1. In a method for electrodepositing aluminum on the surface of a metal or conductive material in an aprotic oxygen and water-free organo-aluminum electrolyte media in the presence of a brightening additive, the improvement which comprises using as said brightening additive a product formed by adding at least one organo-aluminum compound of the general formula $AlR_3$, wherein R is an alkyl radical having from 1 to 4 carbon atoms, to a sulfonamide compound selected from the group consisting of o-benzoic acid sulfonimide, N-benzyolbenzene sulfonimide, di-benzene sulfonimide, benzene-o-disulfonimide and benzene sulfonic acid amide in the presence of inert organic solvent at a temperature not exceeding 100° C., said reaction product containing an aromatic ring substituent and an alkyl group bound to aluminum.

* * * * *